(12) United States Patent
Laudano et al.

(10) Patent No.: US 6,919,676 B2
(45) Date of Patent: Jul. 19, 2005

(54) DISCHARGE LAMP HAVING OVERLAID FLUORESCENT COATINGS AND METHODS OF MAKING THE SAME

(75) Inventors: Joseph D. Laudano, West Haven, CT (US); Prasad S. Sastry, Milford, CT (US); Kamlesh C. Kansal, Fairfield, CT (US)

(73) Assignee: Voltarc Technologies Inc., Waterbury, CT (US)

(*) Notice: Subject to any disclaimer, the term of this patent is extended or adjusted under 35 U.S.C. 154(b) by 32 days.

(21) Appl. No.: 10/462,202

(22) Filed: Jun. 16, 2003

(65) Prior Publication Data

US 2004/0095059 A1 May 20, 2004

Related U.S. Application Data (60) Provisional application No. 60/388,801, filed on Jun. 14, 2002.

(51) Int. Cl.[7] .............................................. H01J 29/10
(52) U.S. Cl. ...................... 313/468; 313/487; 313/493
(58) Field of Search ................................ 313/468, 487, 313/493, 113, 634, 635

(56) References Cited

U.S. PATENT DOCUMENTS

| | | |
|---|---|---|
| 750,554 A | 1/1904 | Potter |
| 1,792,347 A | 2/1931 | Zecher |
| 2,307,502 A | 1/1943 | Gordon et al. |
| 2,407,379 A | 9/1946 | Morehouse |
| 2,916,645 A | 12/1959 | Lemmers et al. |
| 2,932,753 A | 4/1960 | Arnott et al. |
| 3,129,085 A | 4/1964 | Olsen et al. |
| D198,268 S | 5/1964 | Thorington et al. |

(Continued)

FOREIGN PATENT DOCUMENTS

| | | |
|---|---|---|
| DE | 28 37 447 | 3/1979 |
| DE | 43 02 852 A1 | 8/1994 |
| EP | 0 228 737 A2 | 10/1986 |
| JP | 55093649 | 7/1980 |
| JP | 62043454 U | 3/1987 |
| JP | 2119347 U | 9/1990 |
| JP | 4129165 | 4/1992 |
| JP | 6111768 | 4/1994 |

OTHER PUBLICATIONS

International Search Report from PCT Application No. PCT/US03/18781 dated Nov. 5, 2003.

*Primary Examiner*—Vip Patel
(74) *Attorney, Agent, or Firm*—David J. Silvia; Edwards & Angell, LLP (57) ABSTRACT

Disclosed is a new and useful discharge lamp for use in applications, such as tanning and technical lighting, and a method of making the same. The discharge lamp includes, inter alia, a vitreous tube having an axial length, a base phosphor coating applied on the interior of the tube along the entire axial length, and at least one phosphor over-coat applied over the base phosphor coating in one or more axial regions of the vitreous tube. The phosphor over-coat is applied to less than the total length of the vitreous tube. In a representative embodiment, the vitreous tube has an outer periphery which is smooth, but in alternate embodiments, a helical groove path is formed therein over at least a portion of the axial length.

23 Claims, 3 Drawing Sheets

U.S. PATENT DOCUMENTS

| | | | |
|---|---|---|---|
| 3,225,241 A | 12/1965 | Spencer et al. | |
| 3,284,664 A | 11/1966 | Morin et al. | |
| 3,374,381 A | 3/1968 | Albinak et al. | |
| 3,466,443 A | 9/1969 | Roesler et al. | |
| 3,560,786 A * | 2/1971 | Shurgan | 313/493 |
| 3,676,728 A | 7/1972 | Schreurs | |
| 3,717,781 A | 2/1973 | Sadoski et al. | |
| 3,767,956 A | 10/1973 | Bauer | |
| 3,821,578 A | 6/1974 | Beck et al. | |
| 3,988,633 A * | 10/1976 | Shurgan et al. | 313/493 |
| 4,027,191 A | 5/1977 | Schaufele et al. | |
| 4,069,441 A * | 1/1978 | Wanmaker et al. | 313/487 |
| 4,070,598 A | 1/1978 | DeLuca et al. | |
| 4,099,090 A | 7/1978 | Corth et al. | |
| 4,194,125 A | 3/1980 | Wolff | |
| 4,336,479 A | 6/1982 | Kodama et al. | |
| 4,363,997 A | 12/1982 | Kodama | |
| 4,434,385 A | 2/1984 | Touho et al. | |
| 4,499,403 A | 2/1985 | Leppelmeier et al. | |
| 4,591,958 A | 5/1986 | Lamboo | |
| 4,645,969 A | 2/1987 | Hoffman | |
| 4,652,790 A | 3/1987 | Wood | |
| 4,695,757 A | 9/1987 | Ury et al. | |
| 4,703,184 A | 10/1987 | Wolff | |
| 4,731,560 A | 3/1988 | Ernsthausen | |
| 4,794,308 A | 12/1988 | Ernsthausen | |
| 4,825,125 A | 4/1989 | Lagushenko et al. | |
| 4,933,600 A | 6/1990 | Endres | |
| 4,959,551 A | 9/1990 | Schlitt | |
| 4,967,090 A | 10/1990 | Schlitt | |
| 4,978,890 A | 12/1990 | Sekiguchi et al. | |
| 5,008,789 A | 4/1991 | Arai et al. | |
| 5,210,461 A * | 5/1993 | Pai et al. | 313/491 |
| 5,216,323 A | 6/1993 | Baaten et al. | |
| 5,234,710 A | 8/1993 | Dutta et al. | |
| 5,402,036 A | 3/1995 | Ito | |
| 5,557,112 A | 9/1996 | Csoknyai et al. | |
| 5,565,685 A | 10/1996 | Czako et al. | |

* cited by examiner

DISCHARGE LAMP HAVING OVERLAID FLUORESCENT COATINGS AND METHODS OF MAKING THE SAME

CROSS-REFERENCE TO RELATED APPLICATIONS

This application claims priority to U.S. Provisional Application Ser. No. 60/338,801 filed Jun. 14, 2002, which is herein incorporated by reference.

BACKGROUND OF THE DISCLOSURE

1. Technical Field

The present disclosure relates generally to discharge lamps and, more particularly, to a discharge lamp for use in applications, such as tanning or technical lighting, wherein the lamp includes a vitreous tube having overlaid fluorescent coatings applied on an interior thereof to effectuate a desired intensity distribution along the length of the lamp.

2. Background of the Related Art

Discharge lamps have been in existence for many decades. Discharge lamps consist primarily of an elongated vitreous tube having axially opposed end seals. These lamps are coated on the inside with phosphor powders that fluoresce when excited by ultraviolet light. Filament electrodes are mounted on the end seals of the tube and are connected to base pins that engage with the lamp housing. The elongated tube is filled with a rare gas, such as argon, and a drop of mercury.

Discharge lamps typically operate at a relatively low pressure. In operation, an alternating current is applied to the electrodes, which increases the electrode temperature and causes the emission of electrons therefrom. These electrons are accelerated by the voltage across the tube until they collide with the mercury atoms, causing them to be ionized and excited. When the mercury atoms return to their normal state, mercury spectral lines in both the visible and ultraviolet region are generated. The ultraviolet radiation excites the phosphor coating to luminance. The resulting output is not only much higher than that obtained from the mercury lines alone, but also results in a continuous spectrum with colors dependent upon the phosphors used. Typically, the intensity of the ultraviolet radiation emitted from the discharge lamp differs to some degree along the length of the lamp. However, such variation is generally not dramatic, nor are distinct regions of varying intensity created.

In certain lighting applications, such as tanning, it would be advantageous to provide or deliver distinct regions of ultraviolet radiation intensity. Moreover, in technical lighting applications, such as scanning or copying, it would be advantageous to provide a substantially uniform luminous intensity along the length of the lamp. Other needs and opportunities for improvement associated with a range of lighting applications will be apparent from the discussion that follows.

I. Tanning Applications

Since the late 1970s, the practice of tanning, defined as the darkening of one's skin through exposure to ultraviolet (UV) radiation, has increased in popularity in the United States. Each person's skin reacts differently to UV radiation exposure, with the reaction being dependent upon genetically determined factors, such as the amount of melanin pigment already in the skin naturally and the capability of the person's skin to produce additional melanin (facultative pigmentation).

Melanin is the dark pigment found in the retina, hair and skin, except for the palms of the hands, soles of the feet and lips. Without the protection afforded by the melanin pigment, a person's skin would burn when exposed to UV radiation. As stated above, the skin includes naturally occurring melanin pigment and produces additional melanin. Melanin is produced by special cells called melanocytes, which are located deep within the outer layer of the skin. When the melanocytes are stimulated by ultraviolet light, they utilize an amino acid called tyrosine to produce the pigment melanin. Since the melanin pigment is only able to absorb ultraviolet light of approximately 260–320 nanometers, UVB radiation is needed to achieve melanin production. UVA radiation which has a wavelength of approximately 320–400 nanometers can formulate melanin, but only when there is enough photosensitizing material already in the skin to trigger a UVB reaction. With the presence of UVB, melanocytes are stimulated to divide, creating more pigment cells. During this time, the epidermis thickens to form additional protection, a condition referred to as acanthosis.

In the beginning stages of melanin production, the skin has very little melanin or radiation protection capabilities. As a result, UVA radiation is not blocked by melanin pigments and, due to its longer wavelength, penetrates the skin deeper than UVB, causing damage to the corium. Damage to this layer of the epidermis hastens aging and destruction of collagen and connective tissue. A UVA burn can be much more damaging because it is not felt due to its deep penetration.

In order for the pigmentation process to be effective, melanin granules must be oxidized or darkened, which requires a high dose of long-wave UVA. Consequently, exposure to UVB radiation functions to create melanin pigment, while UVA exposure ensures the oxidation of the pigment. Together, the proper combined UV exposure operates to create a light-protection mechanism.

It is well recognized that to obtain the desired uniform tan, a person's facial region often requires the application of more intense radiation than the body region. This is due to the higher levels of melanin pigment present in the face, resulting from a more frequent exposure to the sun than the body. Prior attempts at designing a tanning chamber that provides a more uniform tan have included a lamp assembly that utilizes separate and distinct bulbs in the facial region. More specifically, higher intensity metal halide bulbs are positioned in the facial region and lower intensity bulbs extend over the body.

There is a need therefore, for a discharge lamp for use in applications such as tanning, wherein a single discharge lamp has multiple regions of varying ultraviolet radiation intensity along its length.

II. Technical Lighting Applications

Lighting applications which require a lamp to provide light having a controlled and/or specific luminous intensity or pattern are commonly termed "technical lighting" applications. Document scanning and photocopying are examples of technical lighting applications. These applications require the lamp to provide light having a substantially uniform luminous intensity along its length.

In scanning, a document to be digitally replicated is placed on a glass plate and the housing cover is closed. The scan head, which includes at least two mirrors, a lens, a filter, a charge coupled device (CCD) array and an exposure lamp, is moved slowly across the document by a belt that is attached to a stepper motor. The exposure lamp, which is often a fluorescent discharge lamp, is used to illuminate the document. The exposed image of the document is reflected by a first mirror into a second mirror and then onto the lens.

The lens focuses the image through the filter onto the CCD array. The CCD array converts the reflected image into a data signal, which is then sent to a multifunctional circuit board for image processing (including enlarging, reducing, rotating, etc.). The uniformity of the document exposure by the lamp is critical to the quality of the scanned image. More specifically, the lamp must expose the document to be scanned to a uniform luminous intensity and therefore, the exposure lamp must provide a uniform output along its length.

It is generally well known that the intensity of the ultraviolet radiation and visible light emitted from a discharge lamp decreases from the center towards the ends thereof. The lack of uniformity along the length of the lamp is disadvantageous when the lamp is used in technical lighting applications such as document scanning and photocopying.

U.S. Pat. No. 3,717,781 to Sadoski et al. discloses a discharge lamp which is configured to improved the uniformity of the light output along its length. The Sadoski et al. lamp is an aperture fluorescent lamp. Aperture lamps are those lamps whose brightness is increased by scraping away the phosphor coating along a narrow strip extending the entire length of the lamp. When a reflective layer, such as titanium dioxide, is interposed between the lamp glass wall and the fluorescent phosphor coating, and a narrow strip of this material is scraped away, the brightness of the surface is greatly enhanced. The light output profile of such an aperture lamp also shows a decrease in light intensity at the ends thereof, similar to conventional fluorescent lamps. Sadoski et al. configured the lamp such that the aperture was made wider at the ends of the lamp than at the center, so as to reduce the variation in the light output profile.

The patent literature also includes disclosures concerning aperture lamps wherein the entire outside of the glass tube envelope, except for the aperture, is covered with a reflecting member whose surface area increases towards the ends of the tube. See e.g., U.S. Pat. No. 3,767,956 to Bauer.

As stated above, removing a portion or narrow strip of the phosphor coating creates the aperture. A disadvantage associated with aperture lamps is that removal of the phosphor coating to create the aperture is expensive. Additionally, the brightness of the lamp is dependent on the amount of phosphor coating. Therefore, removal of the phosphor coating beyond a narrow strip reduces the overall brightness of the lamp.

There is a need therefore, for discharge lamps for use in technical lighting applications, such as photocopying or scanning, which cost effectively and without degradation in lamp brightness emit light having a substantially uniform luminous intensity along the length thereof.

There is also need for a method of making discharge lamps for use in applications such as tanning or technical lighting, which, cost effectively and without degradation in lamp brightness, adapts a discharge lamp to emit light having a desired intensity distribution along the length of the lamp. More specifically, there is a need for a method of manufacturing discharge lamps which can readily configure the lamp to provide a luminous output that includes distinct regions of varying intensity along the length of the lamp or an output which is substantially uniform along the length thereof.

SUMMARY OF THE INVENTION

The subject invention is directed to a new and useful discharge lamp which includes, inter alia, a vitreous tube having an axial length, a base phosphor coating applied on the interior of the tube along the entire axial length, and at least one phosphor over-coat applied over the base phosphor coating in one or more axial regions of the vitreous tube. The phosphor over-coat is applied to less than the total length of the vitreous tube. In a representative embodiment, the vitreous tube has an outer periphery which is smooth, but in alternate embodiments a helical groove path is formed therein over at least a portion of the axial length.

In a preferred embodiment, the phosphor over-coat is applied over two axial regions positioned at opposite ends of the vitreous tube. It is envisioned that the two axial regions can have the same axial length or different lengths depending on the intended application for the lamp and the desired intensity profile. The phosphor overcoat(s) applied in each region can be formed from different material and can have a different thickness. In a representative configuration, the two regions of the lamp in which the phosphor over-coat(s) are applied are each adapted and configured for having a luminous output substantially equal to the remainder of the lamp.

In an alternate embodiment, the phosphor over-coat is applied in a single axial region of the vitreous tube. Preferably, in this embodiment, the single axial region has a length of approximately 18 inches and is positioned adjacent to an end of the vitreous tube. However, those skilled in the art would readily appreciate that the length and the location of this region can be adapted to suit the intended application for the lamp. It is presently preferred that the phosphor over-coat be applied in a single region of the tube and be adapted and configured to provide a luminous intensity which is greater than the remainder of the lamp.

Still further, it is envisioned that the discharge lamp, the base phosphor coating and/or the phosphor over-coat(s) include material that fluoresces in the visible light spectrum and the lamp can additionally contain a reflector coating applied on the interior of the tube.

The present disclosure is also directed to a tanning lamp which includes an elongated vitreous tube, a base phosphor coating applied on the interior of the tube and a phosphor over-coat applied to a region of the base phosphor-coated vitreous tube, the over-coated region being adapted for treatment of a user's face.

It is envisioned that at least two regions are defined along the length of the vitreous tube, namely an overcoated region and a non-overcoated region. In a representative embodiment, the overcoated region and the non-overcoated region are adapted to emit light in the visual spectrum, and wherein the same light color is emitted in both the overcoated and non-overcoated regions. In an alternative embodiment, the overcoated region and the non-overcoated region are adapted to emit light in the visual spectrum, and wherein different light colors are emitted in the overcoated and non-overcoated regions. In all of the previously disclosed embodiments, it is envisioned that the phosphor over-coat can be more than one layer of phosphor material.

The present disclosure is also directed to a method for fabricating a discharge lamp having one or more over-coated regions. The method includes the steps of:
  a) washing a vitreous tube with hot water;
  b) drying the washed tube;
  c) applying a phosphor base coat which has a desired UV radiation intensity and to a desired thickness over the full length of the tube;
  d) baking the phosphor base coated tube in a Lehr oven;
  e) applying an over coating of phosphor having a desired thickness to a portion of the tube length which is less than the total length;

f) baking the partially overcoated tube in a Lehr oven;

e) sealing the tube with filament carrying mounts at both ends;

g) dosing the sealed bulbs with a specified amount of mercury;

h) exhausting the tube;

i) filling the tube with a desired gas at a desired pressure; and j) vacuum sealing the mercury-containing tube.

It is further envisioned that the method can include the steps of a) applying a reflector coating to the tube over a desired reflector angle, thickness and length;

b) baking the reflector coated tube in an annealing oven (Lehr) to bake out the phosphor and to vaporize the solvent;

wherein the reflector coat is applied and the coated tube is baked prior to applying the phosphor base coat.

BRIEF DESCRIPTION OF THE DRAWINGS

So that those of ordinary skill in the art to which the subject disclosure pertains will more readily understand how to make and use the lamp and method described herein, preferred embodiments will be described herein with reference to the drawings, wherein.

DESCRIPTION OF PREFERRED EMBODIMENT(S)

Reference is now made to the accompanying figures for the purpose of describing, in detail, preferred and exemplary embodiments of the present disclosure. The figures and accompanying detailed description are provided to describe and illustrate exemplary manners in which the disclosed subject matter may be made and used, and are not intended to limit the scope thereof.

Figure 1:
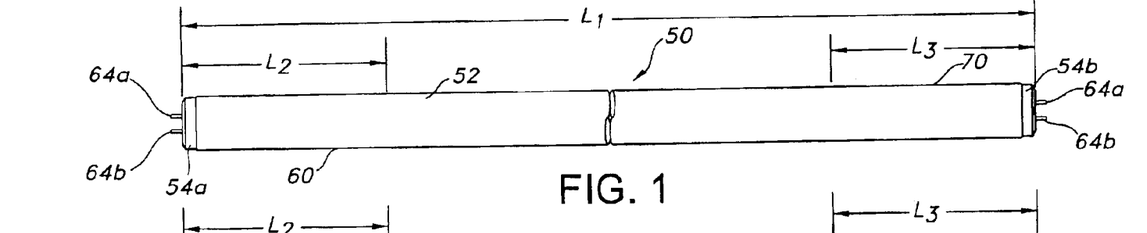
FIG. 1 illustrates a discharge lamp constructed in accordance with an embodiment of the present disclosure having three regions of luminous intensity.

Referring now to FIG. 1, there is illustrated a discharge lamp constructed in accordance with an exemplary embodiment of the present disclosure and designated generally by reference numeral 50. Discharge lamp 50 includes a first region 60 and second region 70, each extending axially along lamp 50. The lengths of the first and second regions 60 and 70 are identified as $L_2$ and $L_3$, respectively. Exemplary lengths $L_2$ and $L_3$ are schematically depicted in FIG. 1; however, lamps fabricated according to the present disclosure may feature first and second regions 60, 70 having different relative lengths, as will be apparent to persons skilled in the art.

Figure 2A:
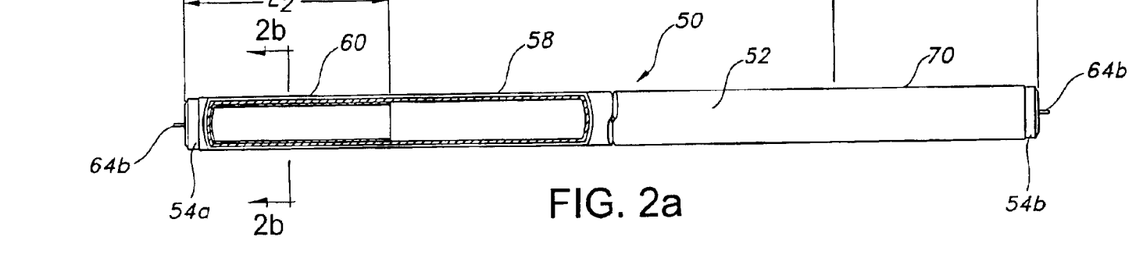
FIG. 2a is a partial cross-sectional view of the discharge lamp of FIG. 1, wherein a portion of the outer periphery of the vitreous tube has been removed to illustrate a region of over-coating having a length of $L_2$.
Figure 2B:
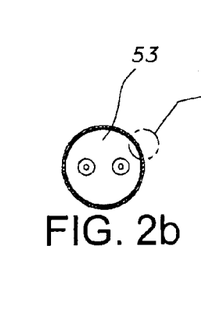
FIG. 2b is a cross-sectional view of the discharge lamp of FIG. 2a, taken along line 2b—2b and illustrating a phosphor base coating and an over-coating applied to the inner surface of the vitreous tube.
Figure 2C:
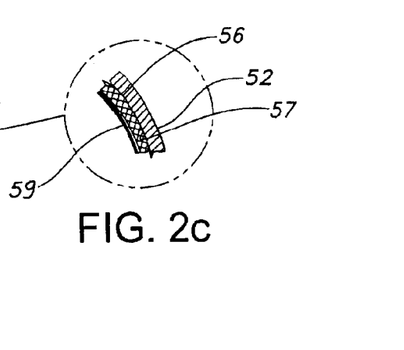
FIG. 2c is an exploded cross-sectional view of the area identified as 2c in FIG. 2b.
Figure 3:
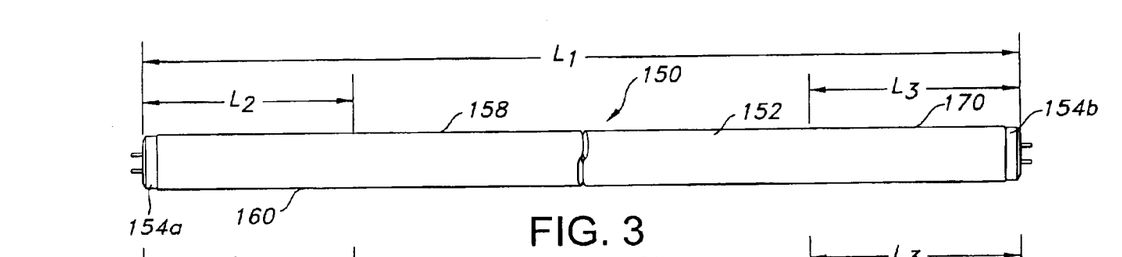
FIG. 3 illustrates a discharge lamp constructed in accordance with an embodiment of the present disclosure having three regions of luminous intensity.

Referring now to FIGS. 2a–2c, exemplary lamp 50 is further illustrated, and includes an elongated vitreous tube 52, first and second end seals 54a and 54b, and first and second electrodes (not shown). Tube 52 has an outer periphery 58 which extends axially between the first and second end seals 54a and 54b. The overall length of tube 52 is identified as $L_1$. In a typical tanning application, the overall length of tube 52 is approximately 72 inches or 6 feet. A first electrode assembly is associated with the first end seal 54a and a second electrode assembly is associated with the second end seal 54b. Each electrode assembly typically includes pins 64a and 64b, which electrically communicate with corresponding electrical contacts associated with a lamp assembly. In an alternate embodiment, pins 64a and 64b can be replaced with a recessed double contact base or any other suitable electrical communication mechanism or arrangement, as will be readily appreciated by those skilled in the art.

Tube 52 has a phosphor base coating 56 applied to interior surface 57 and an over-coating 59, and has a drop of mercury disposed within central core 53. In the embodiment shown herein, phosphor base coating 56 extends over the entire length of tube 52, and over-coating 59 is applied over phosphor base coating 56 only in first and second regions 60 and 70, respectively. Thus, the region between first region 60 and second region 70 includes only a single phosphor coating, namely phosphor base coating 56, whereas first and second regions 60, 70 include both phosphor base coating 56 and over-coating 59. As will be readily apparent to those skilled in the art to which the present disclosure appertains, the length of individual region(s) in which an over-coating is applied, the number and distribution of individual region (s) in which an over-coating is applied, and the thickness and phosphor characteristics of the based coating and over-coating(s) can be selectively adjusted based on the intended lighting application. Additionally, an individual lamp region can include multiple over-coatings and/or a different over-coating material or combination of materials can be applied to each region. Moreover, the thickness of the base coating and/or over-coating(s) may be varied to further achieve desired light application objectives.

In operation, an alternating current is applied to the pins 64a and 64b which increases the temperature of the electrodes and causes the emission of electrons therefrom. These electrons are accelerated by the voltage across the tube 52 until they collide with the mercury atoms, causing them to be ionized and excited. When the mercury atoms return to their normal state, mercury spectral lines in both the visible and ultraviolet region are generated. The ultraviolet radiation excites the phosphor base coating 56 and the over-coating(s) 59 to luminance. The material or materials which are used as over-coating(s) and the thickness thereof are selected so as to adjust and/or control the level of the luminous intensity delivered by individual lamp regions.

For example, in a technical lighting application, material(s) used in an over-coating layer may be selected so that the total luminous output in the over-coated region is substantially equivalent to the rest of the lamp, i.e., the non-overcoated region(s), and thereby, a lamp having a uniform intensity along its length is achieved. In an exemplary tanning application according to the present disclosure, the material(s) used in an over-coating layer may be selected so that the lamp generates a higher intensity UV output and/or has differing UVA/UVB characteristics in the over-coated region(s), e.g., in a region that is to be positioned over the face of the person being tanned.

Additionally, one or all of the coatings applied to interior surface 57 can include material that fluoresces in the visible light spectrum so as to provide light of coloration which is distinct to that region of the lamp. Since the UV radiation produced by the lamp is not visible, it may be desirable in a tanning application, for example, to provide a mechanism for indicating which region of the lamp emits light of an increased intensity, e.g., based on the presence and/or characteristics of the over-coating in such region, and should be positioned over the face of a user.

Thus, the relative positioning and/or relative dimensions of first and second regions 60, 70 may be selected to achieve a variety of lighting application objectives. In a technical lighting application, for example, the first region 60 and second region 70 can be advantageously configured and dimensioned to be positioned over the portion of the lamp which exhibits a falloff in luminous intensity, normally the ends. In a tanning application, the first region 60 can be advantageously configured and dimensioned to be positioned over the facial portion of the person to be tanned and the second region 70 configured and dimensioned to extend for the remainder of the length $L_1$ of the tanning lamp, thereby extending over the chest, torso, legs and feet of the user. In an exemplary tanning lamp embodiment according to the present disclosure, the length of the facial region, i.e., the over-coated region, and thus $L_2$, is approximately 18 inches.

Referring now to FIGS. 3 and 4a–4c, there is illustrated an alternate exemplary embodiment according to the present disclosure, including a discharge lamp designated generally by reference numeral 150. Structural elements of the embodiment shown herein which are similar to those disclosed with respect to the exemplary embodiment of FIGS. 2a–2c are identified by similar reference numerals. As before, discharge lamp 150 includes an elongated vitreous tube 152, first and second end seals 154a and 154b, and first and second electrodes (not shown). Tube 152 has a phosphor base coating 156 applied to interior surface 157 along the entire length thereof and has a drop of mercury disposed within central core 153. Tube 152 has an outer periphery 158 which extends axially between the first and second end seals 154a and 154b. The overall length of tube 152 is identified as $L_1$. The outer periphery 158 of tube 152 includes first region 160 and second region 170 having lengths $L_2$ and $L_3$, respectively. An over-coating 159 is applied so as to overlay phosphor base coating 156 in the first and second regions 160, 170 of tube 152.

Figure 4A:
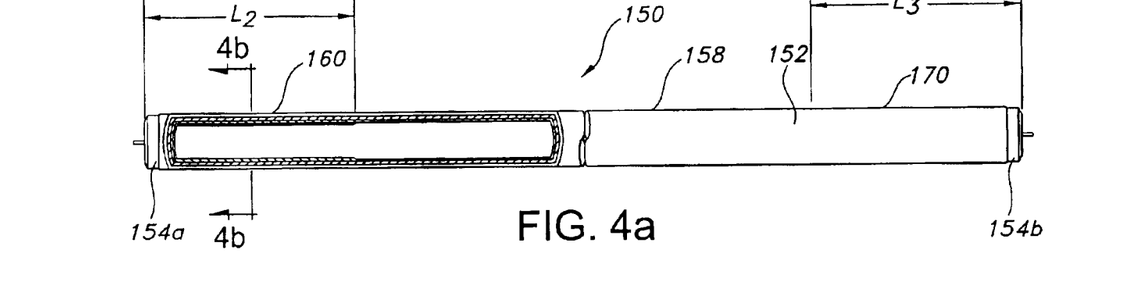
FIG. 4a is a partial cross-sectional view of the discharge lamp of FIG. 3, wherein a portion of the outer periphery of the vitreous tube has been removed to illustrate a region of over-coating having a length of $L_2$ and reflector and base coatings having a length of $L_1$.
Figure 4B:
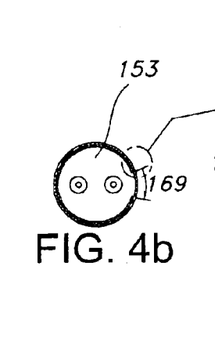
FIG. 4b is a cross-sectional view of the discharge lamp of FIG. 4a, taken along line 4b—4b and illustrating a reflector coating, a phosphor base coating, and an over-coating applied to the inner surface of the vitreous tube.
Figure 4C:
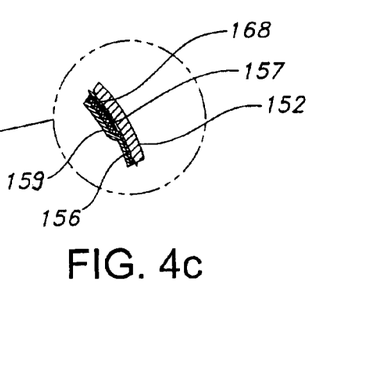
FIG. 4c is an exploded cross-sectional view of the area identified as 4c in FIG. 4b.

In contrast to tube 52 of FIGS. 2a–2c, tube 152 further includes reflective coating 168 which is adapted and configured to direct the ultraviolet radiation generated by lamp 150 in the substantially downward direction through aperture 169 (see FIG. 4b). Reflective coating 168 is positioned adjacent to interior surface 157, is radially outward of phosphor base coating 156, and extends over a portion of the circumference of interior surface 157. Preferably, reflective coating 168 extends over approximately 300 degrees of the circumference of vitreous tube 152, although alternative arrangements of reflective coating 168 may be employed to achieve desired lighting application objectives, as will be apparent to persons skilled in the art. Those skilled in the art would also readily appreciate that over coats may be restricted to only a portion of the circumference of the tube, similar to reflector coating 168.

Figure 5A:
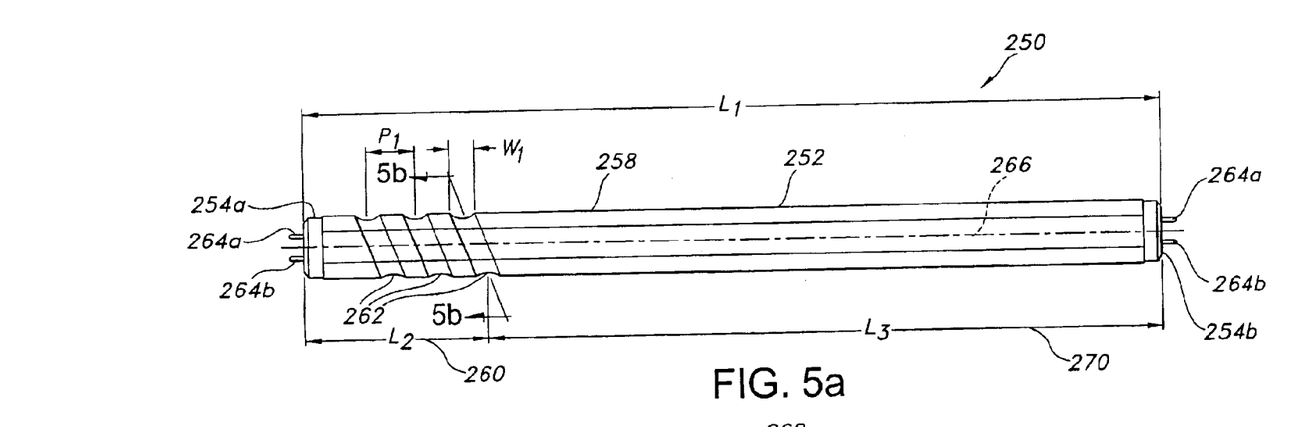
FIG. 5a is an elevational view of a discharge lamp constructed in accordance with an embodiment of the present disclosure, wherein a region of the vitreous tube having a region of length $L_2$ includes an over-coating (not shown) applied to the inner surface and axially spaced apart grooves formed in the periphery.
Figure 5B:
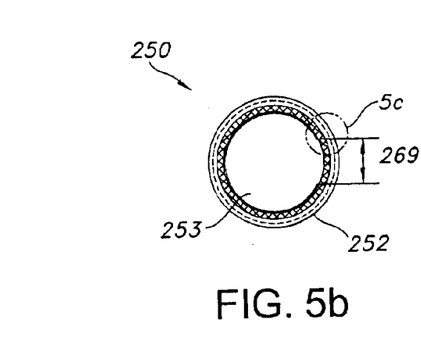
FIG. 5b is a cross-sectional view of the discharge lamp of FIG. 5a, taken along line 5b—5b and illustrating over-coating and groove depth.
Figure 5C:
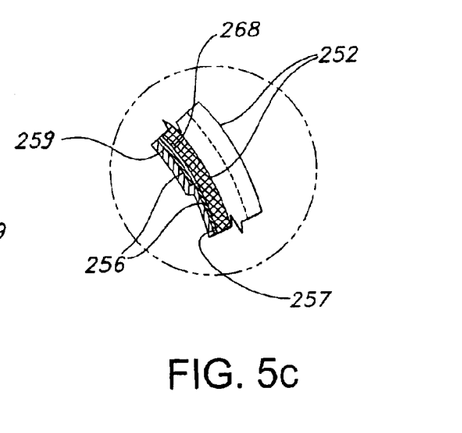
FIG. 5c is an exploded cross-sectional view of the area identified as 5c in FIG. 5b.

Referring now to FIGS. 5a and 5b, there is illustrated a further exemplary embodiment according to the present disclosure, including a discharge lamp designated generally as reference numeral 250. Structural elements of the embodiment shown herein which are similar to those disclosed with respect to the exemplary embodiment of FIGS. 2a–2c are identified by similar reference numerals. As before, discharge lamp 250 includes an elongated vitreous tube 252, first and second end seals 254a and 254b, and first and second electrodes (not shown). Tube 252 has a phosphor base coating 256 applied to interior surface 257 and has a drop of mercury disposed within central core 253. Tube 252 has an outer periphery 258 which extends axially between the first and second end seals 254a and 254b. The overall length of tube 252 is identified as $L_1$.

Tube 252 also includes a first region 260 and second region 270, each extending axially along length $L_1$ of lamp 250 and having lengths $L_2$ and $L_3$, respectively. An over-coating 285, similar to that described with respect to previous embodiments, is applied in first region 260. Unlike the previously described embodiments, however, the first region 260 of lamp 250 has a continuous helical groove path that defines a series of axially spaced apart grooves 262 formed therein, each having a width of $W_1$. It should be noted that, although in the exemplary embodiment shown herein the groove path is continuous, it is envisioned that the groove path can be discontinuous to achieve various lighting application objectives.

Grooves 262 have an axial spacing $P_1$ and are formed in a plane which intersects axis 266 at an acute angle. Due to the presence of grooves 262, a portion of the arc stream which extends between the axially opposed electrodes tends to travel in a generally sinusoidal path in first region 260. As a result, the arc stream length in this region is increased without increasing the length $L_2$ of first region 260. In addition, due to the restriction caused by grooves 262, in this region, the arc stream travels closer to the periphery 258 of tube 252. Each of the foregoing physical properties and conditions advantageously serves to improve the recombination rate of the mercury ions with the phosphor base coating 256 and the over-coating 259. Consequently, the intensity of the ultraviolet radiation in first region 260 is increased and is therefore higher than the UV intensity in second region 270 (all other variables being equal).

It should be noted that the shape (width), size (depth), spacing and orientation (angle) of the grooves can be selectively adjusted in order to achieve a desired intensity within a region. For example, by increasing the depth of grooves 262, thereby bringing the arc stream closer to periphery 258, the intensity in first region 260 is further increased. Also, by orienting the grooves 262 at an angle with respect to axis 266, a larger portion of periphery 258 is deformed than is deformed when the grooves are formed in a plane perpendicular to axis 266. Additionally, when the grooves 262 are angled, the cross-section of periphery 258 is non-circular in the groove locations. The presence of a larger amount of deformed surface area and the non-circular cross-section each further increases the arc stream length and the plasma recombination efficiency adjacent to the phosphor.

As clearly illustrated above, the formation of grooves 262 in first region 260 of tube 252 and the addition of the over-coating 259 separately and in combination enable discharge lamp 250 to provide two distinct and predetermined regions of UV intensity. Additionally, through the adjustment of parameters such as the groove depth, spacing, orientation and width, the intensity of the UV radiation emitted from the first region 260 can be selectively established and/or controlled, both from an absolute sense and on a relative basis as compared to an adjacent region that is devoid of such grooves. More specifically, by adjusting any one or a combination of the above-identified parameters, the desired UV output of first region 260 of lamp 250 can be achieved. It should also be noted that, although the first region 260 is shown in FIG. 4a to be positioned adjacent to first end seal 254a, which is preferable for a tanning application, this region can be positioned anywhere along the length of tube 252. In some applications, for example, it may be desired to have a region of higher intensity located at the center of the tube 252.

A representative method for fabricating discharge lamps having one or more over-coated regions according to the present disclosure is set forth herein below:

1. Wash the glass bulbs with hot water and dry.
2. Apply a reflector coating using the coating equipment and coat the bulbs to the desired reflector angle and thickness. In an exemplary embodiment, apply the reflector coating over the full length of the bulb.
3. Bake the reflector coated bulbs in an annealing oven (Lehr) to bake out the phosphor and to vaporize the solvent.
4. Coat the bulbs with a phosphor base coat which has a desired UV radiation intensity in the desired region(s) and to a desired thickness. In an exemplary embodiment, apply the phosphor base coating over the full length of the bulb.
5. Bake the phosphor base coated bulbs in a Lehr oven.
6. Apply an over coating of phosphor in the desired region(s) and to a desired thickness. In an exemplary embodiment, the over coat is applied at one or both end regions of the lamp, i.e., the over coat extends for a partial length (typically between 16" and 34") from the ends. Thus, the over coat may be applied at one end or both ends and may be of the same or different material (s), the same or different thicknesses, and/or the same or different lengths. Over coats may be of different UV radiation intensity strengths relative to the base phosphor coat (advantageously between 10% and 20% higher than that of base coat UV radiation intensity strength). Over coats may also be of same or different color in the visual color spectrum when the lamps are lit. Over coats may be restricted to only a portion of the circumference of the tube, similar to conventional reflector coats.
7. Bake the bulbs in a Lehr oven again.
8. Seal the bulbs with filament carrying mounts at both ends.
9. Dose the sealed bulbs with a specified amount of mercury.
10. Seal the mercury-containing bulbs and send them through the pumping process which consists of exhausting, processing of filaments and filling the bulbs with required gasses at a designated pressure. The bulbs are then vacuum sealed.
11. Cap the processed lamps using basing cement and solder the filament wires to the pins of the caps.
12. Age the lamps by lighting them using appropriate power supplies for a specific period.

According to the present disclosure, the thickness of the phosphor coating layers are generally not measured directly. Rather, the amount of light transmitted from a standard light source through the phosphor coated tube is typically measured. To facilitate such measurements, a standard coated tube having the coating desired characteristics (based on lamp performance) is fabricated and is used to calibrate a "Light Transmission Reading" (LTR) meter. The standard lamp provides a certain value when measured using the LTR meter.

Thereafter, when a sample tube has been fabricated and the coating thickness is tested to determine if it falls within a prescribed range, the sample tube is tested with the LTR meter and the measured value is compared to the value generated using the standard tube. The LTR meter provides a value for the sample tube that has relevance as a relative measure for comparative purposes, i.e., relative to the value generated by measuring the standard tube. If the coating thickness does not fall within the prescribed range, i.e., it is greater or less than the boundaries of the prescribed range, then it is determined that the coating thickness is not acceptable.

To establish the coating thickness for a sample tube, the following test procedure may be employed:

1. Coat a reflector coating on a clear glass bulb and measure the LTR; adjust the thickness to the desired LTR value by adjusting the viscosity of the reflector phosphor slurry.
2. The same process is used for the phosphor base coat and the overcoat layer(s). Clear glass bulbs are coated separately with base coat and over coat, and LTR measurements are made in each case to establish the thickness of the respective coatings relative to the standard. Adjustments are then made to the base coat phosphor slurry and over coat phosphor slurry, as necessary, by adjusting the viscosity to get the desired LTR values.
3. Once the slurry viscosities have been validated based on the foregoing LTR testing, the actual production ready bulbs are coated with reflector and phosphor slurries according to the exemplary fabrication process described above, i.e., with phosphor slurries having adjusted viscosity levels.

A variety of phosphor coatings may be used according to the present disclosure, as are known in the art. Thus, for example, phosphor coatings that emit primarily in the UVA (315–400 nm) and UVB (280–315 nm) radiation ranges may be advantageously employed in fabricating tanning lamps according to the present disclosure. Exemplary phosphor coatings that may be employed include lead-activated barium disilicate (BSP), cerium-magnesium aluminate (CAM) and/or europium-activated strontium metaborate (SBE). The field of phosphor luminescence materials is well developed, and the advantageous lamps disclosed herein may be fabricated using such materials, including mixtures thereof, as the base and over-coat layers.

While exemplary discharge lamps having multiple intensity regions have been described with respect to various specific embodiments, those of ordinary skill in the art will readily appreciate that various modifications, changes, and enhancements may be made thereto without departing from the spirit and scope of the present disclosure.

What is claimed is:

1. A discharge lamp comprising:
   a) a vitreous tube having an axial length;
   b) a base phosphor coating applied on the tube interior along the entire axial length; and
   c) at least one phosphor over-coat applied over the base phosphor coating in one or more axial regions of the vitreous tube, the phosphor over-coat being applied to less than the total length of the vitreous tube.

2. A discharge lamp as recited in claim 1, wherein the phosphor over-coat is applied over two axial regions of the vitreous tube.

3. A discharge lamp as recited in claim 2, wherein the two axial regions in which the phosphor over-coat is applied are positioned at axially opposed ends of the tube.

4. A discharge lamp as recited in claim 1, wherein the two axial regions in which the at least one phosphor over-coat is applied have different axial lengths.

5. A discharge lamp as recited in claim 1, wherein the phosphor over-coat is applied in a single axial region of the vitreous tube.

6. A discharge lamp as recited in claim 5, wherein the single axial region has a length of approximately 18 inches and is positioned adjacent to an end of the vitreous tube.

7. A discharge lamp as recited in claim 1, wherein the phosphor over-coat(s) applied in each region are formed from different material.

8. A discharge lamp as recited in claim 2, wherein the phosphor over-coat(s) applied in each region of the lamp have a different thickness.

9. A discharge lamp as recited in claim 2, wherein the two regions of the lamp in which the phosphor over-coat is applied are each adapted and configured for having a luminous output substantially equal to the remainder of the lamp.

10. A discharge lamp as recited in claim 5, wherein the phosphor over-coat applied in a single region of the tube is adapted and configured to provide a luminous intensity which is greater than the remainder of the lamp.

11. A discharge lamp as recited in claim 1, wherein the base phosphor coating and/or the phosphor over-coat(s) include material that fluoresces in a visible light spectrum.

12. A discharge lamp as recited in claim 1, further comprising a reflector coating applied on the interior of the tube.

13. A discharge lamp as recited in claim 1, wherein the vitreous tube has an outer periphery having a helical groove path formed therein over at least a portion of the axial length.

14. A tanning lamp comprising:
   a) a vitreous tube of finite length;
   b) a base phosphor coating applied on the interior of the tube;
   c) a phosphor over-coat applied to an axial region of the vitreous tube with a length different than that of the base phosphor coating, the over-coated region providing radiation suitable for tanning a face.

15. A tanning lamp as recited in claim 14, wherein the overcoated region and the non-overcoated region emit light in the visual spectrum, and wherein the same light color is emitted in both the overcoated and non-overcoated regions.

16. A tanning lamp as recited in claim 14, wherein the overcoated region and the non-overcoated region emit light in the visual spectrum, and wherein different light colors are emitted in the overcoated and non-overcoated regions.

17. A tanning lamp as recited in claim 14, wherein the phosphor over-coat includes more than one layer of phosphor material.

18. A tanning lamp as recited in claim 14, wherein the region of the vitreous tube having the phosphor over-coat has a length of approximately 18 inches and is positioned adjacent to an end of the vitreous tube.

19. A tanning lamp as recited in claim 14, wherein the region of the vitreous tube having the phosphor over-coat provides a luminous intensity which is greater than the remainder of the lamp.

20. A tanning lamp as recited in claim 14, further comprising a reflector coating applied on the interior of the vitreous tube.

21. A tanning lamp as recited in claim 14, wherein the vitreous tube has an outer periphery having a helical groove path formed therein over at least a portion of the axial length.

22. A method for fabricating a discharge lamp having one or more over-coated regions, the method comprising the steps of:
   a) washing a vitreous tube with hot water;
   b) drying the washed tube;
   c) applying a phosphor base coat which has a desired UV radiation intensity to a desired thickness over the full length of the tube;
   d) baking the phosphor base coated tube in an annealing oven;
   e) applying an over coating of phosphor having a desired thickness to a portion of the tube length which is less than the total length;
   f) baking the tube in an annealing oven;
   g) sealing the tube with filament carrying mounts at both ends;
   h) dosing the sealed bulbs with a specified amount of mercury;
   i) exhausting the tube;
   j) filling the tube with a desired gas at a desired pressure; and
   k) vacuum sealing the mercury-containing tube.

23. The method as recited in claim 22, further comprising the steps of:
   a) applying a reflector coating to the tube over the desired reflector angle, thickness and length;
   b) baking the reflector coated tube in an annealing oven to bake out the phosphor and to vaporize the solvent;
   wherein the reflector coat is applied and the coated tube is baked prior to applying the phosphor base coat.

* * * * *